(12) United States Patent  (10) Patent No.: US 8,188,427 B2
Kakuta et al.  (45) Date of Patent: May 29, 2012

(54) SCANNING ELECTRON MICROSCOPE ALIGNMENT METHOD AND SCANNING ELECTRON MICROSCOPE

(75) Inventors: Junichi Kakuta, Hitachinaka (JP); Kazuhiro Ueda, Hitachinaka (JP); Tatsuya Maeda, Hitachinaka (JP); Hiroyuki Saito, Hitachinaka (JP); Katsuhiro Sasada, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 523 days.

(21) Appl. No.: 12/182,704

(22) Filed: Jul. 30, 2008

(65) Prior Publication Data

US 2009/0032693 A1    Feb. 5, 2009

(30) Foreign Application Priority Data

Jul. 31, 2007    (JP) .................................. 2007-199488

(51) Int. Cl.
*G01N 23/00* (2006.01)
*G21K 7/00* (2006.01)
(52) U.S. Cl. ......................... 250/310; 250/306; 250/307
(58) Field of Classification Search ................ 250/491.1, 250/310, 306, 307
See application file for complete search history.

(56) References Cited

U.S. PATENT DOCUMENTS

| 5,187,371 | A | * | 2/1993 | Matsui et al. ............. 250/396 R |
| 6,067,164 | A | * | 5/2000 | Onoguchi et al. ............ 356/401 |
| 6,864,493 | B2 | | 3/2005 | Sato et al. |
| 7,511,272 | B2 | * | 3/2009 | Kawada et al. ............... 250/310 |
| 2007/0284542 | A1 | * | 12/2007 | Ogashiwa et al. ......... 250/491.1 |

FOREIGN PATENT DOCUMENTS

JP    2000-195453 A    7/2000

* cited by examiner

*Primary Examiner* — Nikita Wells
*Assistant Examiner* — Johnnie L Smith
(74) *Attorney, Agent, or Firm* — Crowell & Moring LLP

(57) ABSTRACT

A method and apparatus for alignment and astigmatism correction for a scanning electron microscope can prevent an alignment or correction error attributable to the conditions of a particular specimen. First, a difference is determined between optimal values acquired from an automatic axis alignment result on a standard sample, and those obtained from each of a plurality automatic axis alignment results on a observation target sample. An optimal value is then adjusted using the standard sample, by use of the difference thus obtained. Correspondingly, an optimal stigmator value (astigmatism correction signal) is acquired by using the standard sample, and storing the optimal stigmator value as a default value. The optimal stigmator value and the default value depending on the height of an observation target sample pattern are added, and an astigmatism correction is performed on the basis of the resultant stigmator value.

10 Claims, 5 Drawing Sheets

54: Observation sample, 55: Specimen stage

56: Measurement locations, 57: Observation sample

Height (μm)

SCANNING ELECTRON MICROSCOPE ALIGNMENT METHOD AND SCANNING ELECTRON MICROSCOPE

CLAIM OF PRIORITY

The present application claims priority from Japanese application JP 2007-199488 filed on Jul. 31, 2007, the content of which is hereby incorporated by reference into this application.

BACKGROUND OF THE INVENTION

1. Field of the Invention

The present invention relates to a scanning electron microscope (SEM) alignment method and a scanning electron microscope.

2. Description of the Related Art

One factor used to describe capabilities of an SEM is a resolving power. The resolving power indicates the minimum distance between two distinguishable points. For the purpose of acquiring an image with a higher resolving power, it is necessary to align the optical axis of the SEM. The optical axis of the SEM is aligned chiefly through axis alignment and astigmatism correction. Both the axis alignment and the astigmatism correction are performed on a standard sample installed in the specimen stage, or on an observation target sample, for the purpose of reducing work of the operator. Recently-emerging technologies enable an SEM to perform automatic axis alignment and astigmatism correction through its self-evaluation of an optimal condition of its own. For example, Japanese Patent Application Publication No. 2003-22771 (corresponding to U.S. Pat. No. 6,864,493) describes a technology for automatic axis alignment which uses an image processing technology. In addition, Japanese Patent Application Publication No. 2000-195453 describes a technology for detecting misalignment of the optical axis on the basis of change in the path of an electron beam while the electron beam is scanned.

SUMMARY OF THE INVENTION

Indeed, the alignment methods respectively described by Japanese Patent Application Publications Nos. 2003-22771 and 2000-195453 each allow an SEM to accurately identify conditions of the SEM itself, and to perform an automatic alignment on the basis of the identified conditions of the SEM with higher accuracy. However, the following alignment error factors stemming from conditions of the samples remain unresolved.

(1) In a case where an automatic axis alignment is performed by use of both the standard sample and the observation target sample, the difference in height between the two samples makes the two samples have different optimal values for the axis alignment and different optimal values for the astigmatism correction.

(2) In the case of the axis alignment performed on the observation target sample, the irradiation of an electron beam contaminates the observation target sample.

(3) A shape suitable for the axis alignment does not always exist on the observation target sample.

Descriptions will be provided hereinbelow for an axis alignment method and an astigmatism correction method capable of preventing an alignment error and a correction error from occurring particularly due to conditions of a sample, as well as for an SEM for implementing these methods.

A first aspect employed to achieve the foregoing object is to obtain the difference between the optimal value acquired from a result of an automatic axis alignment performed on a standard sample and the optimal values respectively acquired from result of automatic axis alignment performed on a observation target sample, and subsequently to correct the optimal value of the standard sample on which automatic axis alignment is performed by use of one of the differences thus found.

The above-described scanning electron microscope alignment method includes the steps of: performing an axis alignment by use of a standard sample provided on a specimen stage, and thus acquiring an optimal control value for an alignment deflector; performing axis alignments respectively at multiple measurement locations different in height on an observation sample held on the specimen stage, and thus acquiring information on pair each consisting of the height of the measurement location and the optimal control value for the alignment deflector at the measurement location, respectively; and storing a correction curve representing relationships between the heights of the measurement locations and the differences between the optimal control value acquired for the alignment deflector by use of the standard sample and the optimal control values acquired for the alignment deflector by use of the observation sample. This correction curve is previously obtained before an actual specimen is observed.

At the time of observing a specimen, the scanning electron microscope alignment method includes the steps of: performing an axis alignment by use of the standard sample provided on a specimen stage, and thus acquiring the optimal control value for the alignment deflector; measuring the height of the specimen to be observed; acquiring the difference of the optimal control values corresponding to the measured height from the previously stored correction curve; and setting, at the alignment deflector, a value obtained by adding the difference between the optimal control values acquired from the correction curve to the optimal control value acquired for the alignment deflector by use of the standard sample.

The alignment deflector may be a deflector for correcting the misalignment of the optical axis of the objective lens, or a deflector for correcting the misalignment of the optical axis of the astigmatism correction coil. In addition, the correction curve is obtained for each of observing conditions (for example, a condition for an accelerating voltage and an optical condition).

Another scanning electron microscope alignment method includes the steps: performing an astigmatism correction by use of a standard sample provided on a specimen stage, and thus acquiring an optimal control value for an astigmatism correction coil; performing astigmatism corrections respectively at multiple measurement locations different in height on an observation sample held on the specimen stage, and thus acquiring information on pair each consisting of the height of the measurement location and the optimal control value for the astigmatism correction coil at the measurement location, respectively; and storing a correction curve representing relationships between the heights of the measurement locations and the differences between the optimal control value acquired for the astigmatism correction coil by use of the standard sample and the optimal control values acquired for the astigmatism correction coil by use of the observation sample. This correction curve is previously obtained before an actual specimen is observed.

At the time of observing the specimen, the scanning electron microscope alignment method includes the steps of: performing an axis alignment by use of the standard sample provided on the specimen stage, and thus acquiring the optimal control value for the astigmatism correction coil; measuring the height of the specimen to be observed; acquiring the difference between the optimal control values corresponding to the measured height from the previously stored correction curve; and setting, at the astigmatism correction coil, a value obtained by adding the difference between the optimal control values acquired from the correction curve to the optimal control value acquired for the astigmatism correction coil by use of the standard sample. The correction curve is obtained for each of observing conditions (for example, a condition for an accelerating voltage and an optical condition).

In addition, a second aspect employed to achieve the foregoing object is to acquire an optimal stigmator value (or an astigmatism correction signal) by use of the standard sample, to store the optimal stigmator value as a default value, to add the default value depending on the height of a pattern of a observation target sample, and accordingly to perform an astigmatism correction on the basis of a stigmator value obtained by adding the default value.

The above-described axis alignment method enables an automatic axis alignment to be accurately performed by use of only the standard sample, and thus needs no observation target sample for the axis alignment. For this reason, the axis alignment method can always keep the state of the optical axis alignment optimal and stable, that is, keep the apparatus exhibiting its highest resolving power with the apparatus performance being fully demonstrated.

In addition, the above-described astigmatism correction method makes it possible for an astigmatism correction to be performed stably by use of the standard sample regardless of variations such as the height of a specimen.

DESCRIPTION OF THE PREFERRED EMBODIMENT

Figure 1:
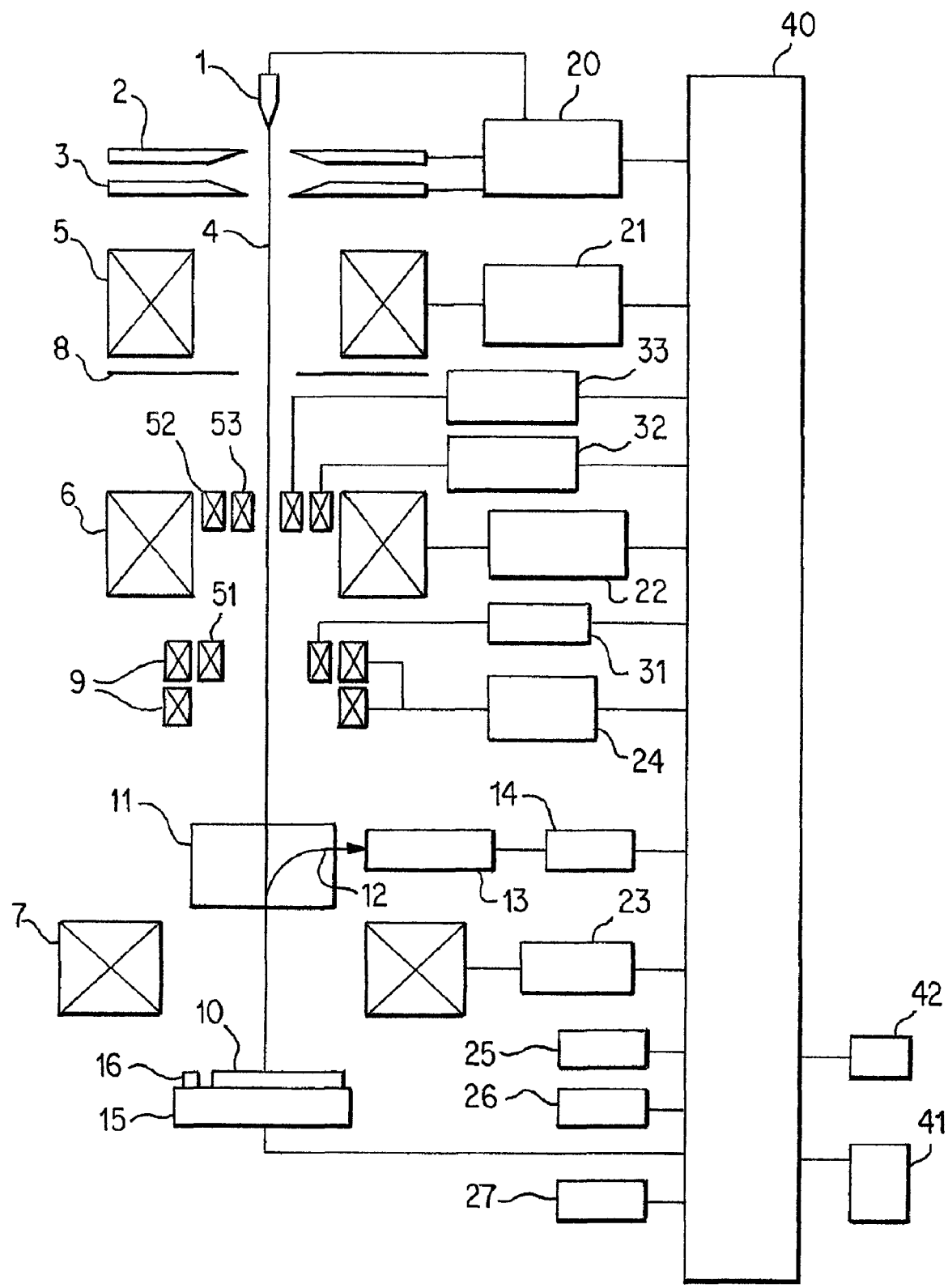
FIG. 1 is a schematic diagram of a scanning electron microscope as an example of the present invention.

FIG. 1 is a schematic diagram of a scanning electron microscope. A voltage is applied between a cathode 1 and a first anode 2 by a high-voltage controlling power supply 20 controlled by a computer 40. Thus, with a predetermined emission current, a primary electron beam 4 is emitted from the cathode 1. An accelerating voltage is applied between the cathode 1 and a second anode 3 by the high-voltage controlling power supply 20 controlled by the computer 40. Thereby, the primary electron beam 4 emitted from the cathode 1 is accelerated, and travels to the rear-stage lens system. The primary electron beam 4 is converged by a converging lens 5 controlled by a lens controlling power supply 21. Subsequently, a diaphragm 8 removes unnecessary ranges from the primary electron beam 4. Thereafter, the resultant primary electron beam 4 is converged into a minute spot on a specimen 10 held on a specimen stage 15 by a converging lens 6 controlled by a lens controlling power supply 22, and by an objective lens controlled by an objective-lens controlling power supply 23. Various types such as an in-lens type, an out-lens type and a snorkel type (or a semi-in-lens type) may be chosen for the objective lens 7.

Furthermore, a retarding type for decelerating a primary electron beam by applying a voltage to a specimen can be also chosen. Moreover, each lens may be constructed by use of an electrostatic lens made of multiple electrodes. A standard sample 16 on which a pattern is formed for axis alignment is provided on the specimen stage 15.

The primary electron beam 4 is two-dimensionally scanned over the specimen 10 by scanning coils 9. The scanning coils 9 are controlled by a scanning-coil controlling power supply 24. A secondary signal 12, such as secondary electron, is generated from the specimen 10 on which the primary electron beam is irradiated. The secondary signal 12 thus generated travels upward through the objective lens 7. Thereafter, the secondary signal 12 is separated from the primary electron by a secondary signal separation cross-electromagnetic field (EXB) generator 11, and the resultant secondary signal 12 is detected by a secondary signal detector 13.

The signal detected by the secondary signal detector 13 is amplified by a signal amplifier 14. Thereafter, the amplified signal is transferred to an image memory 25. The transferred signal is displayed as an image of the specimen on an image display device 26. A single-stage deflection coil 51 (as an objective lens aligner) is arranged in a vicinity of, or in the same location as the scanning coil 9, and operates as an aligner for correcting the misalignment of the optical axis of the objective lens 7. In addition, an astigmatism correction coil 52, made of multiple electrodes, for correcting astigmatism in the X-axis and Y-axis directions is arranged between the objective lens 7 and the diaphragm 8. An aligner 53 (or an astigmatism correction coil aligner) for correcting the misalignment of the optical axis in an astigmatism correction coil is arranged in a vicinity of, or in the same location as the astigmatism correction coil 52. The astigmatism correction coil 52 controlled by the astigmatism-correction-coil controlling power supply 32. An objective lens aligner 51 is controlled by an objective-lens-aligner controlling power supply 31. The astigmatism correction coil aligner 53 is controlled by an astigmatism-correction-coil-aligner controlling power supply 33. An image processing unit 27, a storage 41 and an input device 42 are also connected to the computer 40.

In addition, the scanning electron microscope shown in FIG. 1 is provided with a specimen height measuring sensor (or a z-sensor), which is not illustrated. For example, the z-sensor includes: a light-emitting element for generating a laser beam; a first collective lens for collecting a laser beam emitted from the light-emitting element into a predetermined location (or the location on which the primary electron beam is irradiated) on the specimen; a second collective lens for collecting the laser beam reflected off the specimen; and a position sensor for receiving the laser beam collected by the second collective lens. The height of the specimen is monitored with the use of change in the position on which the position sensor receives the reflected laser beam. Information on the height of the specimen is transferred to the computer 40.

EXAMPLE 1

Figure 2:
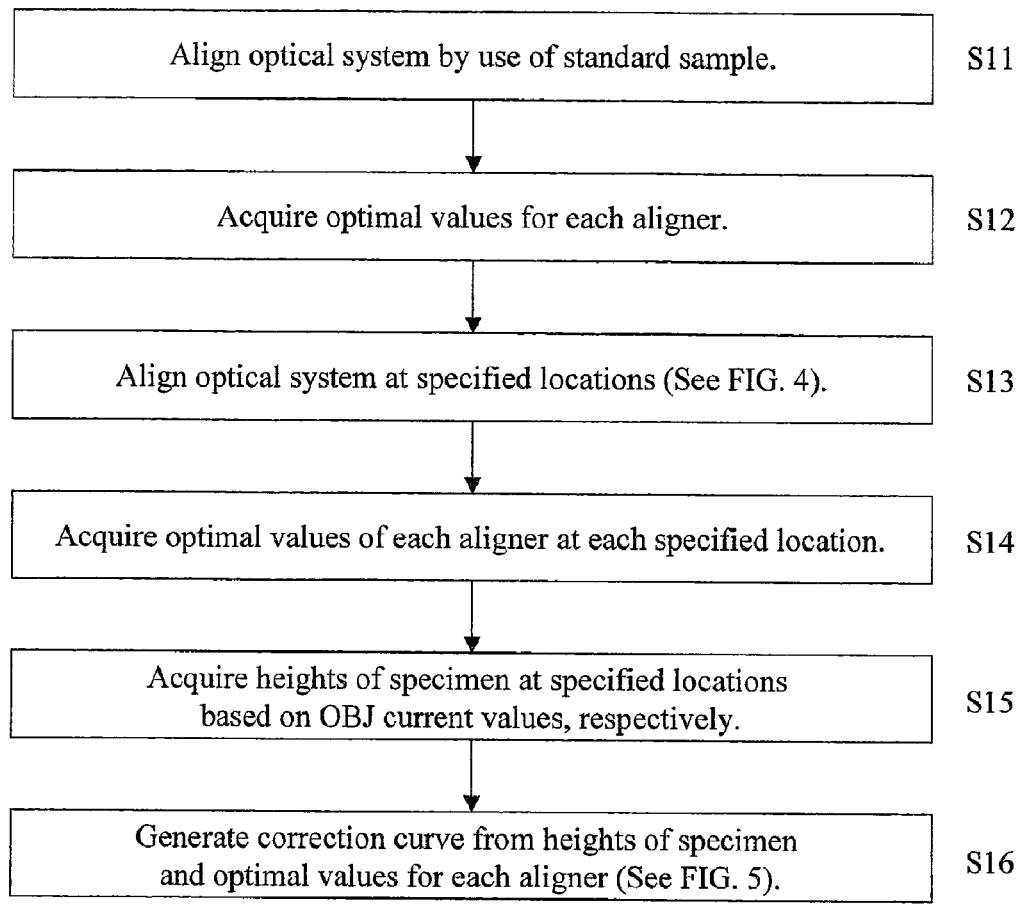
FIG. 2 is a flowchart of processings carried out to acquire a correction curve.

Descriptions will be provided hereinbelow for how to acquire a correction curve necessary for realizing the axis alignment using a flowchart shown in FIG. 2. First of all, an automatic axis alignment is performed by use of the standard sample 16 provided on the specimen stage 15 (in step S11). Thereby, the optimal values of the objective lens aligner 51 in the respective X and Y (A1X1, A1Y1) directions, the optimal values of the astigmatism correction coil aligner 53 in the respective XX, XY, YX and YY (StA1XX1, StA1XY1, StA1YX, StA1YY1) directions, as well as optimal values of the astigmatism correction coil in the respective X and Y (Stx1, StY1) directions are acquired (in step S12).

The automatic axis alignment method is described, for example, in Japanese Patent Application Publication No. 2003-22771.

Figure 4:
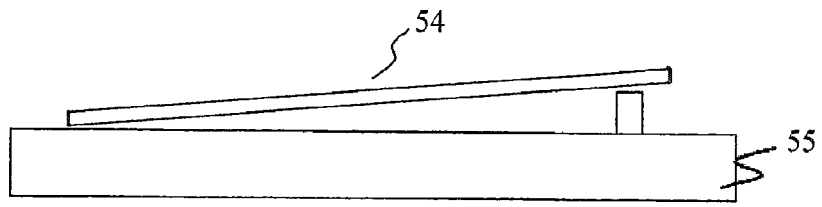
FIG. 4 is a diagram showing a sample inclined for the purpose of acquiring the correction curve.
Figure 5:
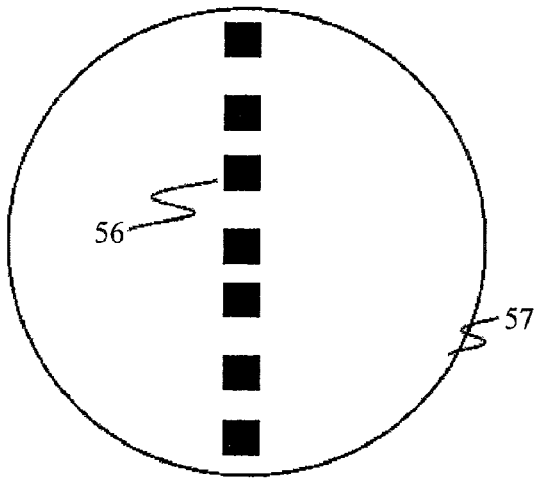
FIG. 5 is a diagram showing locations on a sample which are used to acquire the correction curve.

Subsequently, automatic axis alignments are performed at multiple measurement locations 56 by an observation sample 54 on the specimen stage 15 (in step S13). As shown in FIG. 5, the multiple measurement locations 56 are arranged in a line in an inclination direction on the observation sample 54. As shown in FIG. 4, the heights respectively of the multiple measurement locations 56 are unidirectionally changed. After performing the automatic axis alignments, the optimal values of the objective lens aligner 51 in each of the X and Y (A1X2, A1Y2) directions, the optimal values of the astigmatism correction coil aligner 53 in each of the XX, XY, YX and YY (StA1XX2, StA1XY2, StA1YX2, StA1YY2) directions, the optimal values of the astigmatism correction coil 52 in each of the X and Y (StX2, StY2) directions, as well as the heights at which the respective automatic axis alignments are performed are acquired with the use of current value of objective lens (in steps S14 and S15).

Thereafter, for each aligner, the differences between the optimal value acquired by use of the standard sample 16 and the optimal values acquired by use of the observation sample 54 are acquired as offset values. For example, an offset value of the objective lens aligner 51 in the X direction is expressed with DiffA1X=A1X1−A1X2.

Subsequently, by use of the differences (or the offset values) (for example, DiffA1X) thus acquired and their associated heights acquired from the information on the heights corresponding to the multiple measurement values, a curve is generated as a correction curve (in step S16).

Figure 6:
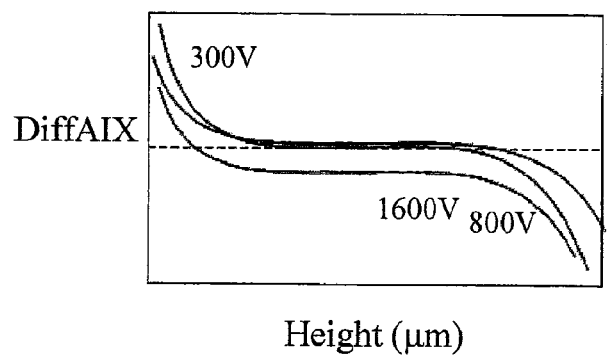
FIG. 6 is a diagram showing examples of an acquired correction curve.

FIG. 6 shows examples of the correction curve. A correction curve is acquired for each of the observation conditions (for example, a used condition for an accelerating voltage and a used optical condition). A correction curve is generated for each of the X and Y directions of the objective lens aligner 51, each of the XX, XY, YX and YY directions of the astigmatism correction coil aligner 53, as well as each of the X and Y directions of the astigmatism correction coil 52. This makes it possible to always keep the state of the optical axis alignment optimal and stable.

Figure 3:
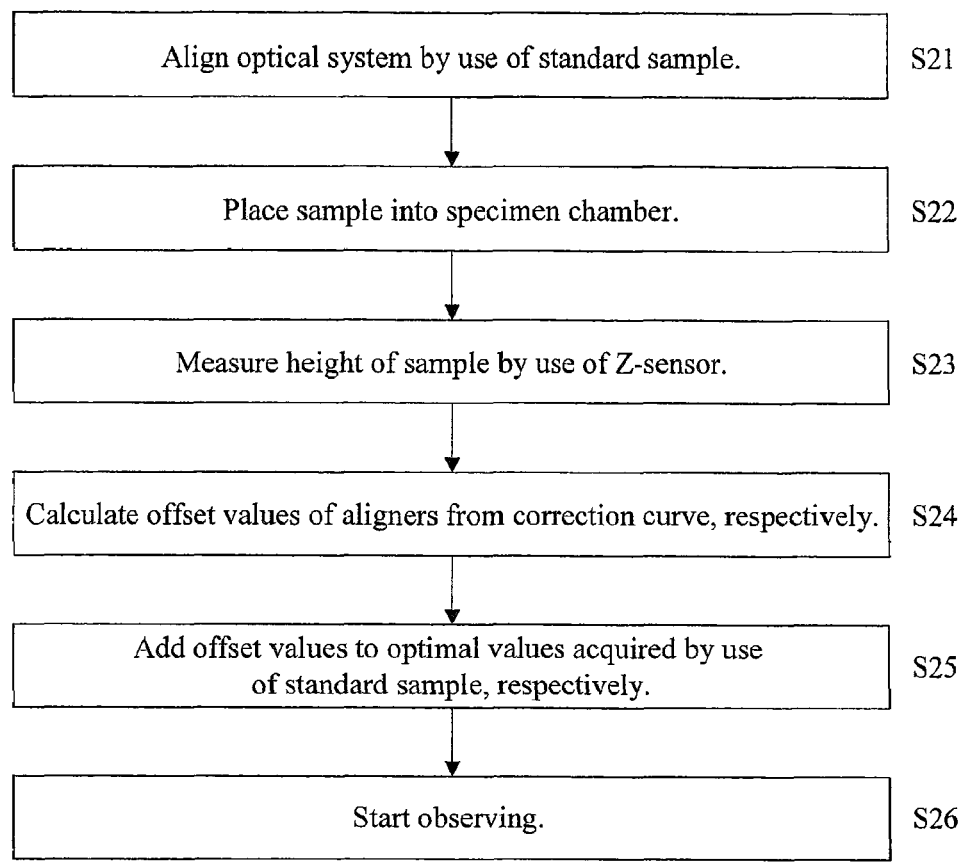
FIG. 3 is a flowchart of processings carries out in an alignment method using the correction curve.

FIG. 3 shows an axis alignment sequence when performing a correction by use of the correction curves while a sample is observed. An automatic axis alignment is performed in advance by use of the standard sample, and thereby the optimal values of each aligner are acquired (in step S21). Subsequently, the observation specimen is placed into a specimen chamber (in step S22). When the observation specimen is placed therein, the height of the observation specimen is measured by use of the height measuring sensor (or the z-sensor) using a laser beam (in step S23). Thereafter, for each of the aligners, the offset values are calculated from the correction curves generated in advance on the basis of the used observation condition and the height measured (in step S24). After that, for each of the aligners, the offset values are added to the optimal value previously acquired for the aligner by use of the standard sample, and the aligner are set at a value obtained through this addition (in step S25). For example, in the case of the X direction of the objective lens aligner, DiffA1X corresponding to the observation specimen is found from the correction curve, and DiffA1X is added to A1X1 acquired in advance by the standard sample. Thereby, the objective lens aligner is set at a value thus obtained as the optimal value in the X direction.

As the individual optimal value, a value of Diff is calculated for each of the X and Y directions of the objective lens aligner, each of the XX, XY, YX and YY directions of the astigmatism correction coil aligner, as well as each of the X and Y directions of the astigmatism correction coil. The foregoing work carried out before placing the specimen in the SEM makes it possible to start to observe the specimen with an accurate axis alignment being completed, and accordingly with the apparatus performance being fully demonstrated after placing the specimen therein (in step S26).

EXAMPLE 2

Figure 7:
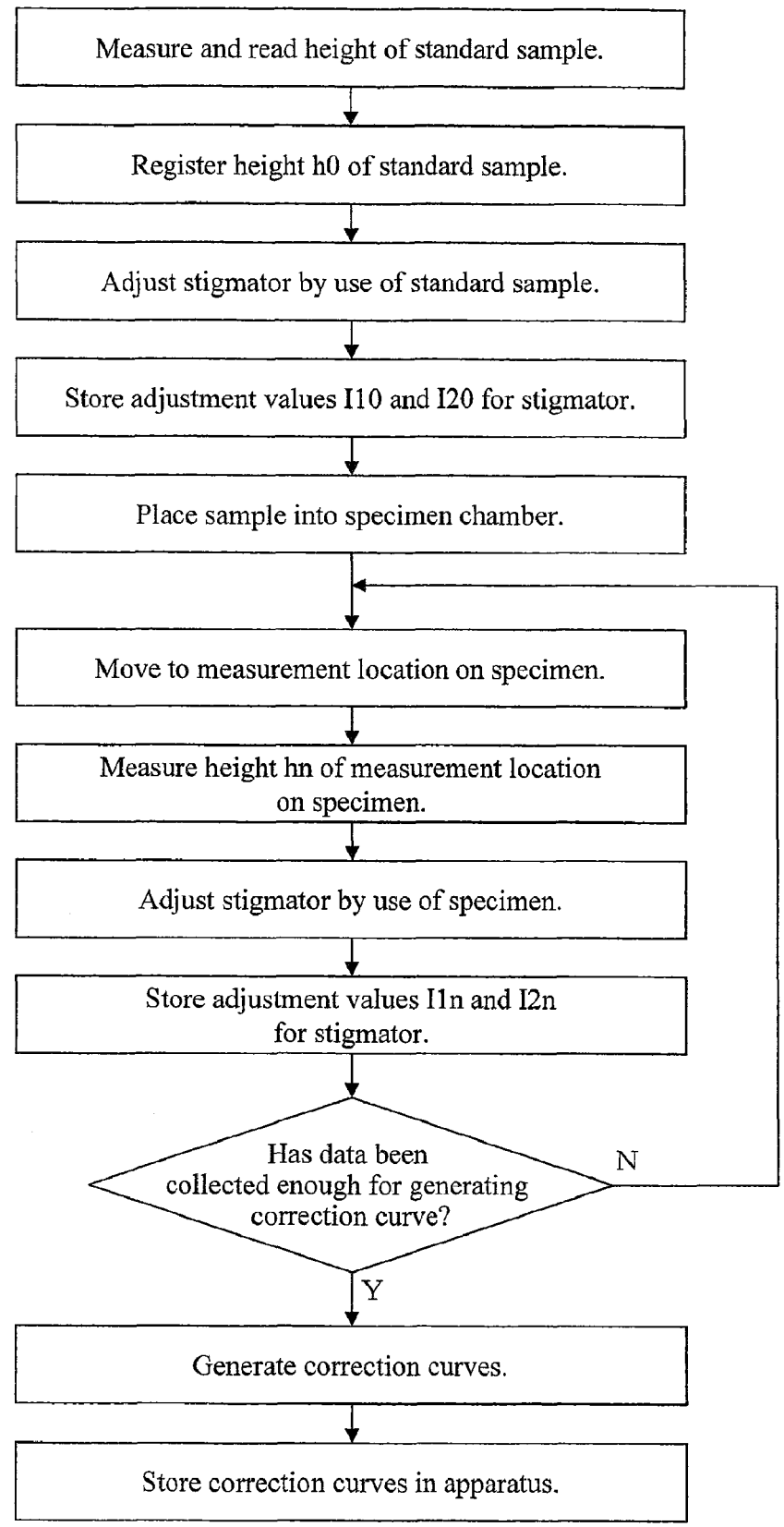
FIG. 7 is a flowchart showing steps carried out for the purpose of generate a correction curve used for an astigmatism correction.

FIG. 7 is a flowchart showing of the steps carried out to generate a correction curve used for performing an astigmatism correction. By use of a standard sample (or a sample for apparatus alignment), optimal stigmator values corresponding to the height of the standard sample (or results of sensing the sample with the z-sensor) are acquired in advance, and are registered as default values. For each focusing condition, these optimal stigmator values are stored as the default values (respectively for the 0°, 45°, 90° and 135° directions) by being uniformly associated with the results of sensing the standard sample with the z-sensor (or LSB values). In the case of the octuple lens obtained by combining two quadruple lens into a single unit, an astigmatism correction is performed on the octuple lens by use of a current I1 supplied to one quadruple lens and a current I2 supplied to the other quadruple lens. For this reason, for each focusing condition, conditions for the currents I1 and I2 (or current values) can be stored in advance as default values.

For each focusing condition, the default values for each direction in which the stigmator is adjusted may be acquired through intentionally varying the heights of the measurement locations different from one another by doing things such as sloping the observation sample as shown in FIGS. 4 and 5. Otherwise, for each focusing condition, the default values may be collected through measuring the heights of the multiple measurement locations on a test sample or the like which is not sloped.

Correction means is designed to add the default values on the actual adjustment values for the stigmator depending on the current values (or the LSB values) of the OBJ (objective lens) which is moved to a desirable location for observation on the wafer. In the case where the objective lens is an electrostatic lens, the voltage values are used instead of the current values. In the case of the foregoing example, with the addition of the stigmator values previously acquired depending on the height of the sample, the astigmatism correction is capable of being performed even in an region where there is no suitable pattern (such as circular or square shape from which components can be easily extracted in each direction) available for the stigmator adjustment. In a region where there exists the above-mentioned pattern, automatic astigmatism correcting functions (for example, AST and high-speed AST), which are termed as recipes, while a wafer is automatically observed and measured, are effective. For this reason, use of the correction means and the automatic astigmatism correcting functions in its proper way makes it possible to correct the stigmator values more effectively.

Particular in a vicinity of an edge of a wafer, there is sometimes no suitable pattern available, for astigmatism correction, having edge orthogonal to the 0°, 45°, 90° or 135° direction although there is a line pattern to be measured. In other words, in some cases, it is desirable that an astigmatism correction should be performed by using a pattern for stigmator adjustment in a region away from an edge of a wafer to some extent, whereas an astigmatism correction should be performed on the basis of the above-described height measurement or the amount of focus control within a range away from the edge of the wafer by a predetermined distance. In such cases, arrangements should be made for the stigmator to be automatically adjusted on the basis of the height of the sample or the like within a range away from the edge of the wafer by the predetermined distance, and for a field of view to be selected for the stigmator adjustment in the vicinity of each measurement location outside the range.

More specifically, when a recipe in which measurement conditions for the scanning electron microscope is recorded is intended to be set up, the stigmator adjustment method is automatically set up as described above in a case where measurement points (MPs) are located within the range away from the edge of the wafer by the predetermined distance, whereas a setup screen is displayed to request an operator to set up locations in the stigmator to be adjusted in a case where the operator intends to set up the MPs outside the range. This configuration makes it possible to reduce work for the operator to perform at the time of setting up the recipe.

In addition, in a case where the observation specimen is a semiconductor device, reference to design data on the semiconductor device makes it possible to determine whether or not there is a suitable pattern available for the stigmator adjustment in a vicinity of each MP depending on where the MP is set up, because the information about each pattern formed on the specimen is registered in design data. When there is a suitable pattern available, the pattern should be displayed as a candidate pattern for the adjustment. When there is no suitable pattern available, it should be displayed that the selection is made for the stigmator adjustment on the basis of the above-described height measurement or the like.

In a case where a pattern for the stigmator adjustment is intended to be selected on the basis of the design data, determination of the selection is made on the basis of whether or not there is a closed pattern satisfying a predetermined condition, and whether or not there are line segments satisfying a predetermined condition, in a field of view (or FOV) which is set up for the SEM with a predetermined magnification being set up therein (or with a magnification needed for the stigmator adjustment being set up therein) within a range away from each MP by a predetermined distance (for example, within a range in which image shift can be performed on the primary electron beam by the deflector).

More specifically, determination of the selection is made whether or not each FOV for the SEM includes a closed pattern (for example, an octagon) having line segments orthogonal to the lines extending in the directions at angles of 0°, 45°, 90° and 135° around the center of the field of view thereof, or whether or not the FOV thereof includes line segments equivalent to those which the closed pattern has.

The foregoing configuration makes it possible to automatically or semi-automatically select the fields of view for the stigmator adjustment without forcing the operator to select the fields of view for the stigmator adjustment in each MP.

Descriptions will be provided hereinbelow of an example for how the stigmator is adjusted on the basis of the measurement of the height of a measurement target wafer.

Specifically, first of all, the height of the standard sample is measured by use of the z-sensor. In a case where the height of the standard sample is registered in advance, this step can be omitted. Subsequently, by use of the standard sample, the stigmator is adjusted. Adjustment values obtained through the stigmator adjustment are stored as I10 and I20. It is desirable that the standard sample used at this time should include a pattern, an octagon for example, whose sharpness can be sufficiently evaluated in the 0°, 45°, 90° and 135° directions. Even if the standard sample is not an octagon, a pattern including line segments equivalent to those of an octagon and a pattern, such as a complete round, whose sharpness can be evaluated in the above-mentioned directions may be substituted for the octagon.

After, as described above, the astigmatism correction is performed by use of the standard sample, an observation target wafer is placed into the specimen chamber. Note that the default value can be acquired by use of the standard sample even after the observation target wafer is placed in the specimen chamber. Subsequently, the height of the sample of the observation target wafer is measured by use of the z-sensor (or the height measuring sensor). Thereafter, an offset amount (LSB value) as the difference between the optimal stigmator value of the standard sample and that of the observation target wafer are calculated on the basis of the measured height of the sample. Subsequently, the offset amount is added on the optimal stigmator value. For example, in the case of the correction coil of the stigmator in the X direction, an offset amount (Diff StigmaX) for the observation target wafer is calculated, and the offset amount (Diff StigmaX) is added on the default value (StigmaX) beforehand acquired. A value obtained through this addition is set up as an optimal stigmator value. This operation is carried out for the correction coil of the stigmator for the Y direction as well.

The foregoing operation is carried out for each of the heights of the respective measurement locations on the sample, and the operation continues to be carried out until the correction curves as shown in FIG. 6 can be generated. Once the correction curves are completed, data on the correction curves is registered in the storage 41. Subsequently, the astigmatism correction is performed on the basis of the data thus registered.

Through carrying out the above-described operation, the optimal stigmator values are set up even when observing and measuring a wafer edge in which astigmatism is apt to shift, or even when observing and measuring a wafer whose height is nonuniform in the surface (for example, a wafer which is so warped with a convex portion or a concave portion being present in the middle of the wafer that the astigmatism and the optical axis shift depending on the measurement location, and a specimen locally or globally charged). This makes it possible to observe the observation target wafer with the apparatus performance being fully demonstrated.

In addition, if the astigmatism correction method is designed to cause the operator to determine, on the basis of the design data of the device or the like, whether to adjust the stigmator on the basis of sharpness of an image or on the basis of the measurement of the height of the specimen, after the sharpness of the image is measured in the four directions, this design makes it possible to set up stigmator conditions for each of the multiple measurement points with ease.

DESCRIPTION OF REFERENCE NUMERALS 1. cathode
2. first anode 3. second anode
4. primary electron beam
5. first converging lens
6. second converging lens
7. objective lens
8. diaphragm
9. scanning coil
10. specimen
11. secondary-signal separating cross-electromagnetic field (EXB) generator
12. secondary signal
13. secondary signal detector
14a. signal amplifier
15. stage
16. axis alignment pattern
20. high-voltage controlling power supply
21. first-converging-lens controlling power supply
22. second-converging-lens controlling power supply
23. objective-lens controlling lens
24. scanning-coil controlling power supply
25. image memory
26. image displaying device
27. image processing unit
31. objective-lens-aligner controlling power supply
32. astigmatism-correction-coil controlling power supply
33. astigmatism-correction-coil aligner controlling power supply
40. computer
51. objective-lens aligner
52. astigmatism correction coil
53. astigmatism correction coil aligner
54. observation sample
55. specimen stage

What is claimed is:

1. A scanning electron microscope alignment method of controlling an alignment deflector for performing an axis alignment, for passing a beam through an axis of a lens, said method comprising the steps of:
performing an axis alignment using a standard sample provided on a specimen stage, based on beam scanning with respect to said plurality of measurement locations, and thus acquiring an optimal control value for an alignment deflector for passing said beam through said axis of the lens;
performing axis alignments at a plurality of measurement locations that differ in height on an observation sample held on the specimen stage, and thus acquiring information comprising a plurality of optimal control values for the alignment deflector for passing said beam through the axis of the lens at the plurality of measurement locations;
storing a correction curve representing relationships between a) changes in the heights of the measurement locations and b) changes in the differences between i) the optimal control value acquired for the alignment deflector by use of the standard sample, and ii) the optimal control values acquired for the alignment deflector by use of the observation sample; and
calculating optimal control values for the measurement locations at which height measurements have been performed, based on the stored correction curve and measured heights of the measurement locations on the specimen.

2. The scanning electron microscope alignment method as recited in claim 1, further comprising the steps of:
performing the axis alignment using the standard sample provided on the specimen stage, and thus acquiring the optimal control value for the alignment deflector;
measuring the height of a specimen to be observed;
acquiring from the previously stored correction curve, a difference value that corresponds to the measured height; and
setting, at the alignment deflector, a value obtained by adding the difference value acquired from correction curve to the optimal control value acquired for the alignment deflector by use of the standard sample.

3. The scanning electron microscope alignment method as recited in claim 1, wherein:
the alignment deflector corrects misalignment of the optical axis of an objective lens.

4. The scanning electron microscope alignment method as recited in claim 1, wherein:
the alignment deflector corrects misalignment of the optical axis of the astigmatism correction coil.

5. The scanning electron microscope alignment method as recited in claim 1, wherein
the correction curve is acquired for each of various observing conditions.

6. A scanning electron microscope alignment method of controlling an astigmatism correction coil that corrects an astigmatism of an electron beam emitted from an electron source, said method comprising the steps of:
performing an astigmatism correction using a standard sample provided on a specimen stage, and thus acquiring an optimal control value for an astigmatism correction coil, for passing said beam through an axis of a lens of said scanning electron microscope;
performing astigmatism corrections at a plurality of measurement locations that differ in height on an observation sample held on the specimen stage, based on beam scanning with respect to said plurality of measurement locations, and thus acquiring information comprising a plurality of optimal control values for the astigmatism correction coil for passing said beam through the axis of the lens at the plurality of measurement locations;
storing a correction curve representing relationships between a) changes in the heights of the measurement locations and b) changes in the differences between i) the optimal control value acquired for the astigmatism correction coil by use of the standard sample, and ii) the optimal control values acquired for the astigmatism correction coil by use of the observation sample; and
calculating optimal control values for the measurement locations at which height measurements have been performed, based on the stored correction curve and measured heights of the measurement locations on the specimen.

7. The scanning electron microscope alignment method as recited in claim 6, comprising the steps of:
performing the axis alignment using the standard sample provided on the specimen stage, and thus acquiring the optimal control value for the astigmatism correction coil;
measuring the height of the specimen to be observed;
acquiring from the previously stored correction curve, a difference value that corresponds to the measured height; and
setting, at the astigmatism correction coil, a value obtained by adding the difference value acquired from the correction curve to the optimal control value acquired for the astigmatism correction coil by use of the standard sample.

8. The scanning electron microscope alignment method as recited in claim 6, wherein
the correction curve is acquired for each of various observing conditions.

9. A scanning electron microscope comprising:
an electron source;
a deflector for aligning an axis of an electron beam emitted from the electron source such that it passes through an axis of the optical element;
a controller for controlling the deflector; and
a height measuring sensor for measuring the height of a measurement location to be irradiated with the electron beam;
wherein the controller performs an axis alignment at said measurement location, based on i) the height of the measurement location that has been measured by the height measuring sensor, and ii) a previously stored correction curve that represents a relationship between a) the height of the measurement location and b) deflection condition of the deflector.

10. A scanning electron microscope comprising:
an electron source;
astigmatism correction coil for correcting an astigmatism of an electron beam emitted from the electron source;
a controller for controlling the stigmator; and
a height measuring sensor for measuring the height of a measurement location to be irradiated with the electron beam;
wherein the controller performs an astigmatism correction at said measurement location based on i) the height of the measurement location that has been measured by the height measuring sensor, and ii) a previously stored correction curve that represents a relationship between a) the height of the measurement location and b) operating settings of the astigmatism correction coil.

\* \* \* \* \*